United States Patent [19]

Sweeney, Jr.

[11] Patent Number: 5,821,400
[45] Date of Patent: Oct. 13, 1998

[54] SATUROMETER

[76] Inventor: John Worth Sweeney, Jr., P.O. Box 3369, Stony Creek, Conn. 06405

[21] Appl. No.: 769,471

[22] Filed: Dec. 20, 1996

Related U.S. Application Data

[63] Continuation of Ser. No. 601,569, Feb. 14, 1996, abandoned, which is a continuation of Ser. No. 819,757, Jan. 13, 1992, abandoned.

[51] Int. Cl.$^6$ ...................................................... G01N 7/10
[52] U.S. Cl. ........................................ 73/19.05; 73/19.12
[58] Field of Search ............................... 73/19.05, 19.01, 73/19.1, 19.12

[56] References Cited

U.S. PATENT DOCUMENTS

| | | | |
|---|---|---|---|
| 4,222,277 | 9/1980 | Kurtz et al. | 73/721 |
| 4,563,892 | 1/1986 | D'Aoust | 73/19.05 |
| 4,662,210 | 5/1987 | D'Aoust | 73/19.05 |

*Primary Examiner*—Michael Brock
*Attorney, Agent, or Firm*—St. Onge Steward Johnston & Reens LLC

[57] ABSTRACT

The present invention is a saturometer capable of directly measuring Delta P. The saturometer is also capable of providing measurements of temperature and barometric pressure as well as calculating percent saturation. The saturometer is further provided with a liquid crystal display for displaying the above measurements and calculation. The sensor package is removably housed in a probe having either an hour-glass shaped or auger/screw shaped interior designed to increase the velocity of water flow over the sensor package, thereby increasing the accuracy of the measurements.

6 Claims, 5 Drawing Sheets

SATUROMETER

This is a continuation of application Ser. No. 08/601,569 filed Feb. 14, 1996 now abandoned, which is a continuation of Ser. No. 07/819,757 filed on Jan. 13, 1992 now abandoned.

BACKGROUND OF THE INVENTION

The present invention relates to saturometer instruments, and more specifically but not by way of limitation to a hand-held, battery powered instrument for measuring the saturation levels of gases dissolved in water.

Excesses of total dissolved gases, known as supersaturation, in streams, lakes, and fish rearing facilities has been identified as a cause of both chronic and acute health problems for wild and cultured fish. Supersaturation occurs naturally under certain conditions, but it may, also, be inadvertently produced by dams or other structures that alter water flow. Additionally, in the hatchery, certain practices intended to enhance the quality of water—such as oxygenation—may actually cause unacceptably high levels of saturation, unless steps are taken to maintain the total gas saturation at 100%. Almost any excess of dissolved gases can be stressful to aquatic life, and if that level becomes high enough it can cause gas embolisms resulting in the death of the fish life. Thus, the saturation of total dissolved gases, which is the sum of the partial pressures of all the dissolved gases, should be routinely monitored. As a result, instruments capable of measuring the total dissolved gas pressure have been developed.

One such system is described in U.S. Pat. No. 4,662,210 issued to D'Aoust for a "MULTIPLE PARAMETER TEMPERATURE, DISSOLVED GAS AND ATMOSPHERIC PRESSURE MEASURING METHOD AND APPARATUS". D'Aoust comprises a probe coupled to a control box having a display. The D'Aoust probe comprises an absolute pressure sensor connected to a thin walled gas permeable tubing. Dissolved gas molecules enter the gas permeable tubing and create pressure against an absolute pressure sensor, thereby providing a reading of the total dissolved gas pressure. Additionally, the D'Aoust probe provides measurements of barometric pressure and temperature. The above measurements are communicated to the control box for display. The D'Aoust device also displays the difference between the dissolved gas and barometric pressures (Delta P). D'Aoust determines Delta P by measuring both the total gas pressure and the barometric pressure, and then subtracting the barometric pressure from the total gas pressure. However, because the D'Aoust device determines Delta P from two measured absolute pressures, it is subject to inaccurate results. That inaccuracy occurs because in using two gauges, D'Aoust introduces the two error margins of the gauges into the calculation of Delta P. Additionally, each gauge must be separately calibrated which introduces a second source of error. A third source of error is introduced because Delta P is a small quantity—normally between 1–40 mm Hg—when compared to both the total gas pressure and the barometric pressure. For example, typical barometric pressure sensors have a tolerance of 1%. At one atmosphere (760 mm Hg), an error of up to 8 mm Hg can be expected. Thus, when Delta P is calculated the error introduced by the barometric pressure sensor could be as large or larger than the value of Delta P. Any slight error in the measurement of the total dissolved gas pressure and the barometric pressure will skew the calculation of Delta P.

Accordingly, the Saturometer of the present invention has been designed to directly measure Delta P. The present invention employs a novel probe and differential pressure gauge which allows it to directly measure Delta P, thereby eliminating the calculation errors encountered by the prior art.

SUMMARY OF THE INVENTION

The present invention comprises an analyzer connected to a sensor package by a cable assembly. Additionally the present invention comprises water channeling probes. In use, the sensor package is connected to one of the three available probes and placed in the water.

The sensor package comprises a gas permeable tubing sealed at one end with the other end being in contact with one side of the diaphragm of a differential pressure gauge. Dissolved gas molecules entering the gas permeable tubing exert pressure on one side of the diaphragm of the differential pressure gauge to provide a measurement of the total gas pressure. The other side of the diaphragm of the differential pressure gauge is referenced to the ambient air through a tube to provide that side of the differential pressure gauge with a signal corresponding to barometric pressure. The differential pressure gauge determines the difference between the total gas pressure and the barometric pressure to provide a signal representative of Delta P. The sensor package is further provided with a temperature sensor. Upon measurement, the sensor package delivers signals representing Delta P and temperature to the analyzer.

The analyzer comprises an LCD display which is controlled by a set of selector switches corresponding to a quantity to be displayed. The displayed quantities are Delta P, temperature, barometric pressure and percent saturation. A fifth switch is provided as the analyzer on/off switch. The analyzer is constructed with a waterproof housing. However, there is a small opening on one side of the housing which is covered with a sheet of gas permeable membrane which allows the pressure inside of the analyzer to always be at equilibrium with the pressure of the atmosphere. Thus, the analyzer is provided with a barometric pressure gauge to measure the barometric pressure for display on the LCD display.

Once the sensor package is connected to a probe, both the sensor package and probe are placed in the water. To increase the accuracy and efficiency of the sensor package, water flow across the surface of the sensor must occur. Without water flow, as the dissolved gases migrate into the permeable tubing, there develops a pressure gradient that extends from the surface of the tubing outward into the boundary layer of the water. The effect of that gradient is to lower the energy of the active diffusion process, and hence to slow the rate of permeation of the gases through the permeable tubing. Thus, water flow is necessary to sweep away the boundary layer of water, thereby improving the rate of permeation.

In still water, the temperature sensor is also affected because a heat gradient develops at the surface of the sensor and extends into the boundary layer of the water. The effect of that gradient is to dramatically increase the time required for the temperature sensor to come to equilibrium with the average temperature of the ambient water.

Accordingly, a user of the present invention must move the sensor package and probe through the water manually if the water is not flowing. Thus, the hand-held probe of the present invention must be repeatedly lifted and lowered to create a water flow over the sensor package.

To more efficiently channel the flow of water directly over the sensor surfaces, the present invention is provided with a probe which locates the sensors, meaning both the permeable tubing of the gas collector and the temperature sensor, in an open tube. Specifically, the present invention employs a Bernoulli tube which has an internal hour-glass shape instead of a straight sided tube. That shape will produce a venturi effect when the Bernoulli tube is pulled through the water, meaning that if the permeable tubing is located in the waist of the hour-glass, then the velocity of the water flowing across it will be greater than if a straight sided tube were used.

A second design of the probe which is even more efficient than the first, is to shape the inside surface of the Bernoulli tube into an auger or screw so that as water flows through the tube it flows in spiral pattern. The cumulative effect of that design attribute is to make a longer path for the water to flow through as it passes through the auger Bernoulli tube. That means the velocity of the low of water across the permeable tubing is significantly increased.

Furthermore, because of the augured shaped of the inside of the probe, a lateral vector is introduced into the water flow as it swirls through the tube, and that relatively turbulent flow is still more effective at removing the stagnant layer of water at the surface of the sensors.

As the probe and sensor package are moved, water is channeled across the temperature sensor and gas permeable tubing allowing the temperature to be measured and dissolved gas molecules to enter the gas permeable tubing. The gas molecules exert pressure on one side of the diaphragm of the differential pressure gauge. The opposite side of the diaphragm of the pressure gauge experiences atmospheric pressure delivered from the small tube exposed to the ambient air. The strain gauge takes those two pressures to develop a signal representing their difference which is equal to Delta P. The sensor package then communicates the temperature and Delta P signals to the analyzer for a user selected display. The analyzer also measures the barometric pressure and calculates the percent saturation for display to the user selected signal on its a liquid crystal display. The analyzer calculates the percent saturation by adding Delta P to the barometric pressure and dividing by the barometric pressure and multiplying that result by one hundred ((DP+BP)/BP*100).

DETAILED DESCRIPTION OF THE PREFERRED EMBODIMENT

Figure 1:
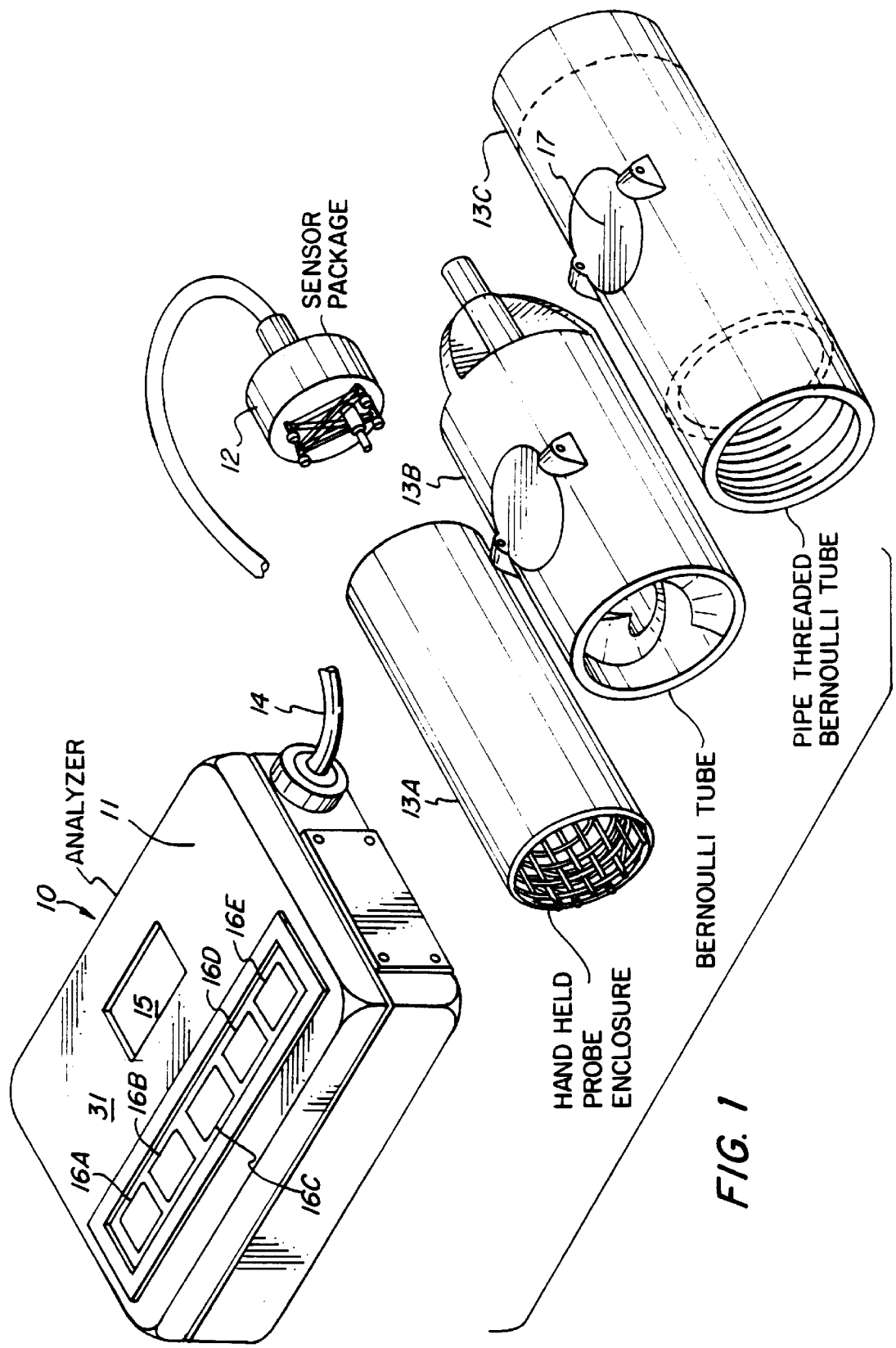
FIG. 1 is a perspective view of the analyzer, sensor package, and three probes.

The configuration of saturometer 10 is shown in FIG. 1. Saturometer 10 comprises analyzer 11, sensor package 12, and detachable probes 13A–C. The outer container of analyzer 11 is comprised of waterproof housing 31. However, there is a small opening (not shown) on one side of housing 31 which is covered with a sheet of gas permeable membrane, which allows the pressure inside of analyzer 11 to always be at equilibrium with the pressure of the atmosphere. Analyzer 11 is further provided with a barometric pressure gauge 32 (FIG. 7) which provides a signal representing barometric pressure for display on LCD display 15. Analyzer 11 receives signals of Delta P and temperature from sensor package 12 (discussed herein) through cable assembly 14 for display on LCD display 15. Analyzer 11 is provided with selector switches 16A–E because LCD display 15 only displays one quantity at a time. Selector switch 16E is the power on/off switch for analyzer 11. To display a quantity, a system user depresses one of selector switches 16A–D resulting in that quantity being displayed on LCD display 15. In the preferred embodiment, selector switches 16A–E are key pad switches, however, any comparable switch means could be substituted.

For operation, sensor package 12 is attached to one of probes 13A–C. If probe 13C is to be used, sensor package 12 is fitted into holder 17 which exposes the sensors to a water flow. Probe 13C has a Bernoulli tube configuration and is used in a situation where there is sufficient water flow. In that instance, the sensor package and probe are lowered into the water and let rest or probe 13C is screwed onto an outflow pipe using its threads so that the water will flow through probe 13C and across sensor package 12.

Probe 13B is a Bernoulli tube used to create a water flow in relatively still waters. The design and construction of probe 13B will be discussed herein with reference to FIGS. 3–6.

If probe 13A is to be used, sensor package 12 is fitted into its rear, and probe 13A and sensor package 12 are then manually moved through water. Probe 13A is a straight tube causing water flow against sensor package 12 as it is moved vertically through the water.

Figure 2:
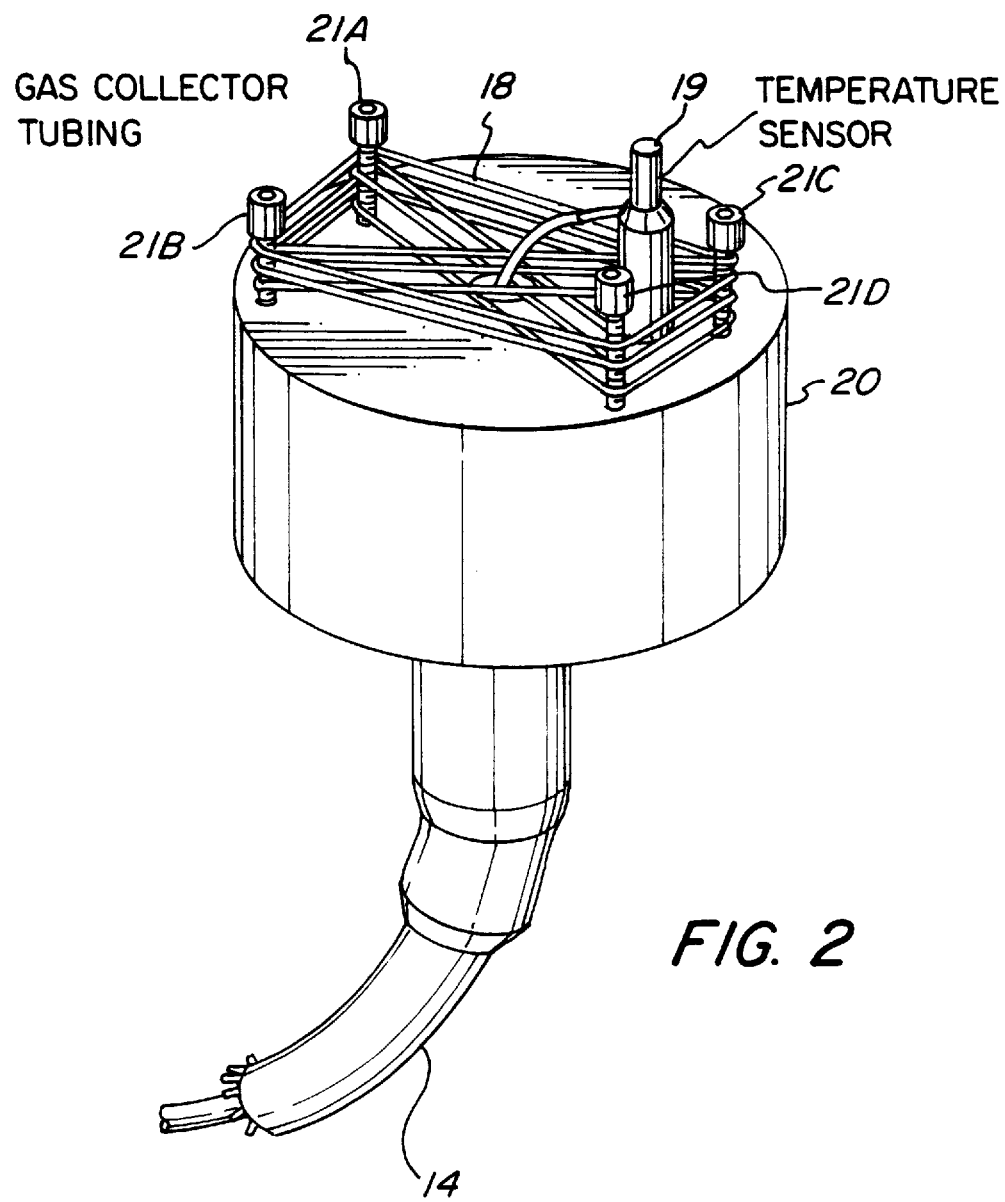
FIG. 2 is a perspective view of the sensor package.

Referring to FIG. 2, sensor package 12 will be described. Sensor package 12 comprises gas permeable tubing 18, temperature sensor 19, and housing 20 which houses a differential pressure gauge (not shown). Gas permeable tubing 18 is sealed at one end and wound about posts 21A–D with its opposite end terminating in contact with one side of the diaphragm of the differential pressure gauge. Gas molecules enter the gas permeable tubing and exert a pressure against the diaphragm representative of the total dissolved gas pressure. The opposite side of the diaphragm of the differential pressure gauge is connected to a tube (not shown) which runs through cable assembly 14 and terminates in analyzer 11, thereby exposing the diaphragm to atmospheric pressure. Thus, the pressures on the opposite sides of the diaphragm create a differential signal which is Delta P. That signal is communicated to analyzer 11 via cable assembly 14. Additionally, sensor package 12 measures the temperature which is also communicated to analyzer 11 via cable assembly 14.

In the preferred embodiment of the present invention, the gas permeable tubing is a silastic tubing; however any comparable gas permeable tubing could be substituted. Additionally in the preferred embodiment, the gas permeable tubing may be thirty inches or less and is filled with a non-permeable solid or fluid. That non-permeable solid or fluid remains inside the membrane to decrease the internal volume, thereby increasing the ratio of the surface area to the internal volume, which increases the rate and accuracy of the measurement of Delta P.

In the preferred embodiment, the barometric pressure gauge is not mounted inside sensor package 12. However, the inside of sensor package 12 could be waterproofed and placed in communication with the atmosphere via a tube similar to the one connected to the back of the differential pressure gauge. That would allow the inside of sensor package 12 to be pressurized to atmospheric pressure. Thus, an absolute pressure gauge could be mounted in sensor package 12 to measure the barometric pressure for communication and display by analyzer 11.

Figure 3:
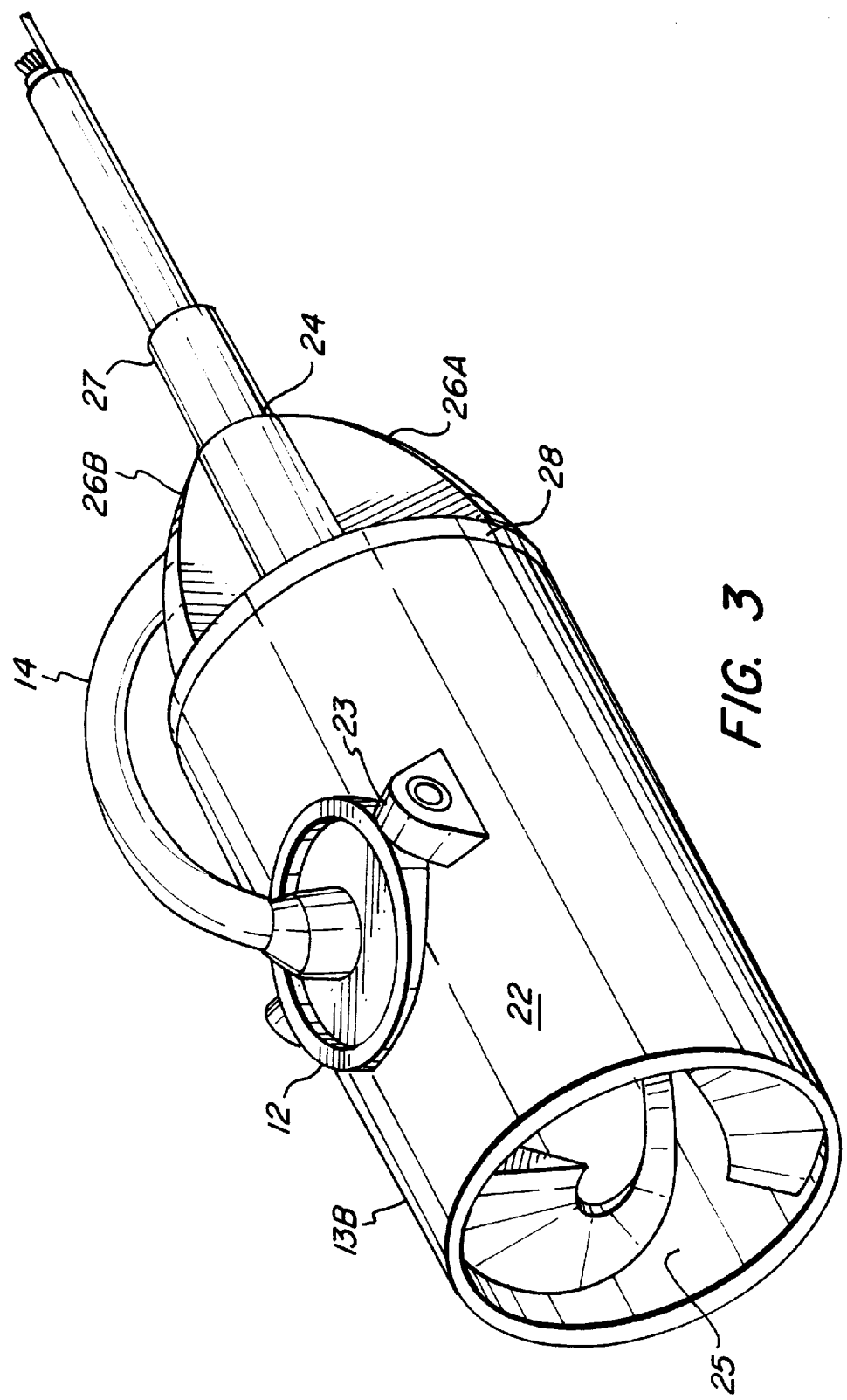
FIG. 3 is a perspective view of the auger shaped Bernoulli tube probe showing the sensor package mounted in the probe.

With reference to FIGS. 3–6, the structure and function of probe 13B will be described. To provide accurate measurements of Delta P and temperature, it is necessary to create a rapid flow of water across sensor package 12. Probe 13B and C are designed to maximize that water flow. Probe 13B (FIG. 3) comprises tube 22 having on its outside holder 23. Holder 23 allows sensor package 12 to fit inside tube 22 for maximum flow as shown in FIG. 3. Once sensor package 12 is fitted into tube 22, cable assembly 14 is routed through vaned bell housing 24 and back to analyzer 11. That configuration allows probe 13B to be moved vertically through the water with the water flow passing through vaned bell housing 24 across sensor package 12 and out opening 25.

Figure 6:
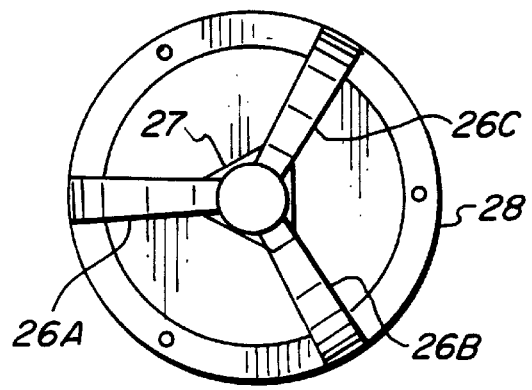
FIG. 6 is a top view of the vaned bell housing of the Bernoulli tube probe.

Vaned bell housing 24 (FIG. 6) comprises vanes 26A–C secured at one end by stem 27 and having their opposite ends mounted on ring 28 as shown in FIG. 6. That configuration allows the water to be efficiently channeled into probe 13B.

Figure 4:
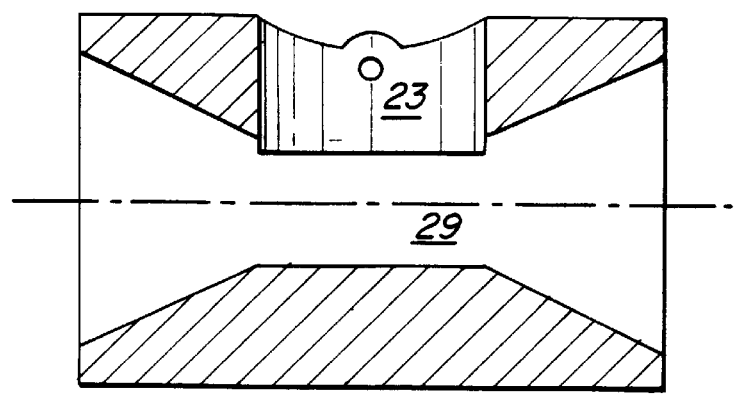
FIG. 4 is a cut-away side view of the Bernoulli tube probe showing the hour-glass shape of one embodiment.
Figure 5:
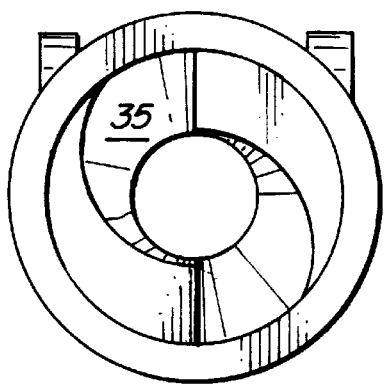
FIG. 5 is a front view of the Bernoulli tube probe showing the augured or screw shape of a second embodiment.

One embodiment of probe 13B is shown in the cross-sectional drawing of FIG. 4. Sensor package 12 fits into holder 23 which positions gas permeable tubing 18 and temperature sensor 19 in the center of hour-glass opening 29. The hour-glass shape of probe 13B creates an increased flow of water across sensor package 12, thereby increasing the accuracy of measurements.

A second embodiment of probe 13B is shown in FIG. 6. In that embodiment, inside surface 35 of probe 13B is augured or screw shaped so that the water flows through the probe in a spiral pattern. The auger or screw shaped design of probe 13B makes the water flow path longer, thereby increasing the velocity and intensity of the water flow across sensor package 12.

Although probes 13A–C have been described for the purposes of disclosure for use in determining the saturation of dissolved gases in water, one of ordinary skill in the art will readily recognize that any sensor requiring a flow of liquid could be used in the probes. Additionally, each of probes 13A–C could be used in any substance (e.g. ammonia or beer) to create a flow across a sensor package to measure the saturation of the liquid or any other desired measurement.

Figure 7:
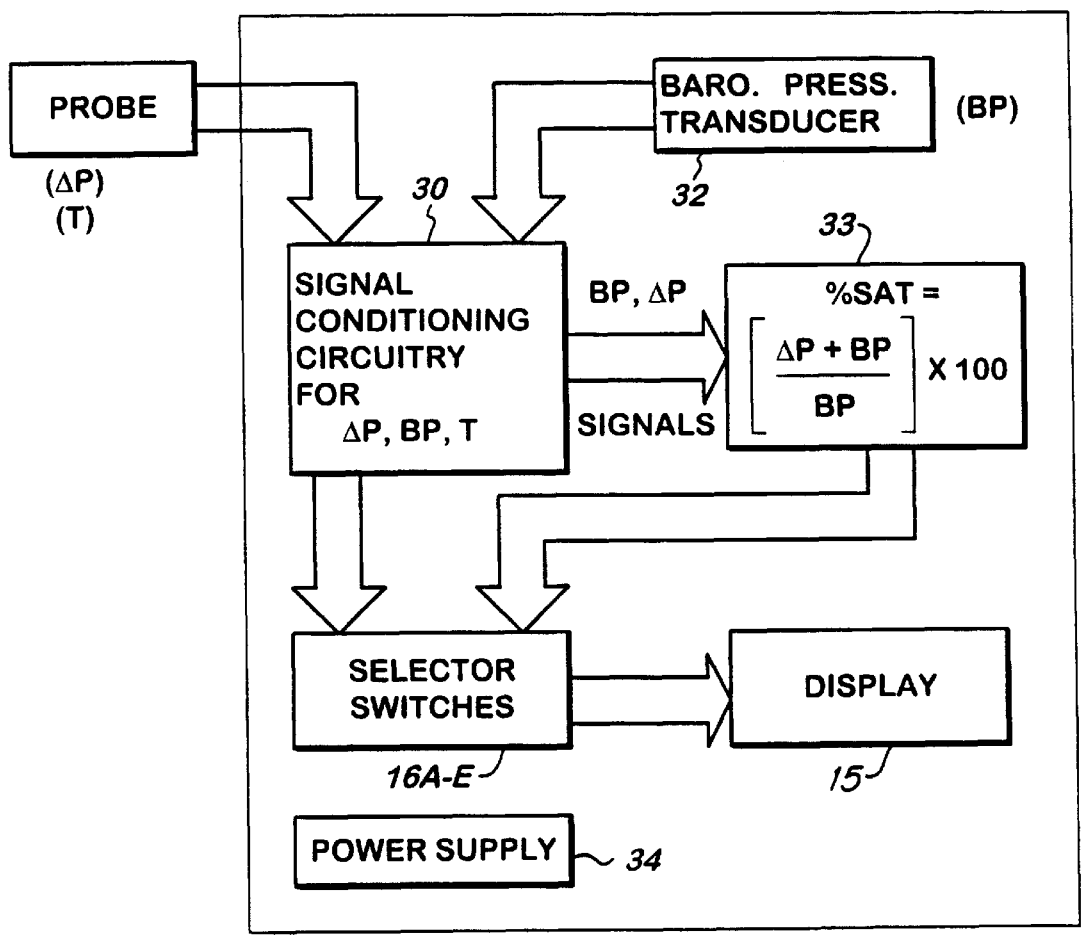
FIG. 7 is a block diagram of the probe and analyzer of the preferred embodiment of the present invention.

With reference to FIG. 7, the operation of saturometer will be described. Sensor package 12 is connected to one of probes 13A–C and then lowered into the water for measurement taking. As the probe is manually moved through the water, sensor package 12 measures Delta P and temperature and communicates those two signals to signal conditioning circuit 30 of analyzer 11. Barometric pressure gauge 32 provides a signal representing barometric pressure to signal conditioning circuit 30. Signal conditioning circuit 30 ensures that the differential pressure gauge, temperature sensor and barometric pressure transducer are properly calibrated. Signal conditioning circuit 30 is a resistive network which sets the output of the differential pressure gauge and barometric pressure transducer to zero when a true zero pressure signal is measured. Signal conditioning circuit 30 also adjusts the value of the signal sent to LCD display 15. That signal is in millivolts and must be converted to the appropriate units before display (e.g. mm Hg). Analyzer 11 is further provided with percent saturation calculation circuit 33. Percent saturation calculation circuit 33 receives the Delta P and barometric pressure signals from signal conditioning circuit 30, adds Delta P with barometric pressure, then divides by the barometric pressure, and multiplies that value times one hundred to determine the percent saturation ((DP+BP)/BP*100). For display, the user depresses one of selector switches 16A–D, and the quantity corresponding to the selected switch, either Delta P, barometric pressure, temperature, or percent saturation, is displayed on liquid crystal display 15. Analyzer 11 is further provided with power supply 34 to provide power for liquid crystal display 15 through on/off switch 16E.

While the preferred embodiments of the present invention have been described for the purposes of this disclosure, changes in the design and arrangements of features may be made by those skilled in the art, which changes are encompasses within the spirit of this invention as defined by the appended claims.

I claim:

1. A saturometer, comprising:

pressure sensing means capable of directly measuring Delta P, the difference between the total gas pressure in a liquid and barometric pressure;

a probe removably connected to said sensing means for channeling water across said sensing means, said probe comprising a tube open at both ends having an outer wall and an inner hour-glass shaped chamber wherein said outer wall has an opening which extends to said inner hour-glass shaped chamber; and a display means in communication with said sensing means for displaying Delta P.

2. The probe according to claim 1, further comprising a vaned bell-housing connected to one end of said tube to channel said liquid into said inner hour-glass shaped chamber.

3. The probe according to claim 1, said tube further having threads at one end.

4. A saturometer, comprising:

pressure sensing means capable of directly measuring Delta P, the difference between the total gas pressure in a liquid and barometric pressure;

a probe removably connected to said sensing means for channeling water across said sensing means, said probe comprising a tube open at both ends having an outer wall and an inner auger or screw shaped chamber wherein said outer wall has an opening which extends to said inner auger or screw shaped chamber; and a display means in communication with said sensing means for displaying Delta P.

5. The probe according to claim 4, further comprising a vaned bell-housing connected to one end of said tube to channel said liquid into an inner hour-glass shaped chamber.

6. The probe according to claim 4, said tube further having threads at one end.

* * * * *